(12) United States Patent
Lihl et al.

(10) Patent No.: US 7,104,666 B2
(45) Date of Patent: Sep. 12, 2006

(54) COOLING CHAMBER AND SYSTEM OF A COOLING CHAMBER WITH A MICROTOME

(75) Inventors: Reinhard Lihl, Vienna (AT); Siegfried Tanki, Stegersbach (AT); Michael Zimmermann, Leopoldsdorf (AT)

(73) Assignee: Leica Microsysteme GmbH, Vienna (AT)

( * ) Notice: Subject to any disclaimer, the term of this patent is extended or adjusted under 35 U.S.C. 154(b) by 84 days.

(21) Appl. No.: 10/711,406

(22) Filed: Sep. 16, 2004

(65) Prior Publication Data

US 2005/0078471 A1    Apr. 14, 2005

(30) Foreign Application Priority Data

Oct. 7, 2003   (DE) ................. 103 46 996

(51) Int. Cl.
  *F21V 33/00*   (2006.01)
(52) U.S. Cl. .................. 362/89; 362/294; 362/800; 83/520; 83/915.5
(58) Field of Classification Search ................. 362/89; 359/390; 83/520, 915.5
See application file for complete search history.

(56) References Cited

U.S. PATENT DOCUMENTS

| | | | | |
|---|---|---|---|---|
| 4,284,894 A | * | 8/1981 | Sitte et al. | ............... 250/443.1 |
| 4,532,838 A | * | 8/1985 | Soderkvist | ..................... 83/13 |
| 4,625,608 A | * | 12/1986 | Behme et al. | ................ 83/713 |
| 5,070,935 A | * | 12/1991 | Sitte et al. | ..................... 165/61 |
| 5,871,271 A | * | 2/1999 | Chien | ......................... 362/106 |
| 6,178,757 B1 | * | 1/2001 | Sitte et al. | ..................... 62/126 |
| 2004/0035275 A1 | | 2/2004 | Lihl et al. | ..................... 83/520 |
| 2005/0072285 A1 | * | 4/2005 | Lang et al. | .................... 83/520 |

* cited by examiner

*Primary Examiner*—Renee Luebke
*Assistant Examiner*—Zahra I Bennett
(74) *Attorney, Agent, or Firm*—Simpson & Simpson, PLLC

(57) ABSTRACT

A cooling chamber 10 for a microtome 1 is disclosed. A knife 2 having a cutting edge 16 is arranged in the cooling chamber 10 opposite a sample holder 4 having a sample 4a retained therein. The microtome 1 further possesses a stereomicroscope 12 having an optical system 14, the optical system 14 defining an optical axis 11. The region of the sample 4a and of the cutting edge 16 of the knife 2 is observable with the stereomicroscope 12. There is mounted in the cooling chamber 10 an illumination system 20 that emits light 20a and is directed onto a surface 2a of the knife 2 in such a way that the light 20a reflects from the surface 2a parallel to the optical axis 11.

16 Claims, 3 Drawing Sheets

COOLING CHAMBER AND SYSTEM OF A COOLING CHAMBER WITH A MICROTOME

CROSS REFERENCE TO RELATED APPLICATIONS

This application claims priority of the German patent application 103 46 996.6, filed Oct. 7, 2003, which is incorporated by reference herein.

FIELD OF THE INVENTION

The invention concerns a cooling chamber for a microtome. Additionally the invention concerns a system of a cooling chamber with a microtome.

BACKGROUND OF THE INVENTION

The microtome with the designation Leica Ultracut UCT, on which the Leica FCS cooling chamber is mounted, has two illumination systems as standard equipment. Fluorescent lamps are mounted outside the chamber next to the objective of the stereomicroscope, and serve to illuminate the cut sections. The second illumination system is positioned, by means of light guides, directly beneath the knife. The bright gap produced by this illumination is helpful as the knife and specimen are brought close to one another.

The model MTX and MTXL microtome of the RMC company has an illumination system that is equipped similarly to the illumination system of the Leica company's microtome. Since the illumination of the fluorescent lamps is not sufficient, a fiber optic illumination system is offered as an accessory. Two goosenecks placed to the left and right of the knife are usual.

As already mentioned, illumination by means of fluorescent lamps has too little intensity to produce good visibility of the cut sections in the stereomicroscope. The illumination using a fiber optic system, on the other hand, can be brought very close to the knife and has sufficient intensity, but on the one hand it interferes with manipulation when the sections are removed from the knife, and on the other hand illumination with the fiber optic system causes ice crystals.

These ice crystals are produced because cooling chambers for ultramicrotomes are operated with liquid nitrogen. The liquid nitrogen produces nitrogen gas, which fills the chamber. Continuous formation of this gas causes it to flow steadily out of the cooling chamber. This continuous flushing with dry gas prevents the entry of moist air and thus the formation of ice deposits, with no need for a cover on the chamber (which is open at the top).

If, however, objects such as the fiber optic system are inserted from outside into the chamber, they penetrate through the boundary layer between the cold nitrogen gas and the air at room temperature. These objects introduce heat into the cold region and cause turbulence, and the cold gas no longer flows out steadily. Turbulence at the boundary layer with the moist air results in the precipitation of small ice crystals, which then also settle on the knife and reduce the service life of a knife between cleanings.

SUMMARY OF THE INVENTION

It is therefore the object of the present invention to create a cooling chamber with which optimum illumination and reliable handling of cut sections is possible.

This object is achieved, according to the present invention, by a cooling chamber comprising an illumination system that emits light, a knife surrounded by the cooling chamber, wherein the knife defines a surface, and a stereomicroscope provided outside the cooling chamber for the observation of the surface of the knife, whereby the illumination system is arranged such that the emitted light is directed onto the surface of the knife in such a way that the light reflects from the surface toward the stereomicroscope.

It is a further object of the invention to create system a cooling chamber with a microtome or ultramicrotome with which optimum illumination and reliable handling of the cut sections is possible.

This object is achieved, according to the present invention, by a system of a cooling chamber with a microtome, comprising a knife defining a cutting edge, a sample holder, wherein the is knife and the sample holder are arranged in the cooling chamber and opposite to each other, a stereomicroscope positioned on the microtome wherein the stereomicroscope defines an optical axis, and the region of the cutting edge of the knife being observable with the stereomicroscope, and an illumination system mounted in the cooling chamber emits light which is directed onto a surface of the knife in such a way that the light reflects from the surface toward the stereomicroscope.

The use of light-emitting diodes as the illumination system has the advantage that they emit only a small amount of heat and therefore cause no turbulence in the nitrogen gas. Light-emitting diodes have a small emission angle. Several light-emitting diodes can illuminate the knife in directed fashion, and result in a high intensity. Good visibility of the cut sections with the stereomicroscope is thus achieved at high magnifications. Depending on the arrangement and segmentation of the light-emitting diodes, the cut sections can be illuminated both laterally and perpendicularly. Operation of segments of the arrangement of light-emitting diodes makes possible, for example, oblique illumination or only frontal illumination. It has been found that light-emitting diodes are functional down to a temperature of approximately −160° C. The arrangement according to the present invention of the light-emitting diodes in the cooling chamber ensures that the temperature does not fall below this value.

The illumination system provided in the cooling chamber is mounted so that the emitted light is directed onto a surface of the knife, and so that the light is reflected from the surface toward the optical system of the stereomicroscope. According to a further embodiment, the illumination system is arranged in the cooling chamber in such a way that the light of the illumination system reflects substantially parallel to the optical axis.

As already mentioned above, it is particularly advantageous if the illumination system is constructed from several light-emitting diodes (LEDs). Segments of the several LEDs can then be capable of being switched on and off individually in order to implement an oblique illumination of the surface of the knife.

According to a preferred embodiment, the illumination system is constructed from a first, a second, a third, a fourth, and a fifth LED. An oblique illumination of the surface of the knife can be implemented, for example, with the first and the second LED or also with the fourth and the fifth LED.

BRIEF DESCRIPTION OF THE DRAWINGS

Further advantages and advantageous embodiments of the invention are the subject matter of the Figures below and the descriptions thereof. In the individual Figures.

DETAILED DESCRIPTION OF THE INVENTION

Figure 1:
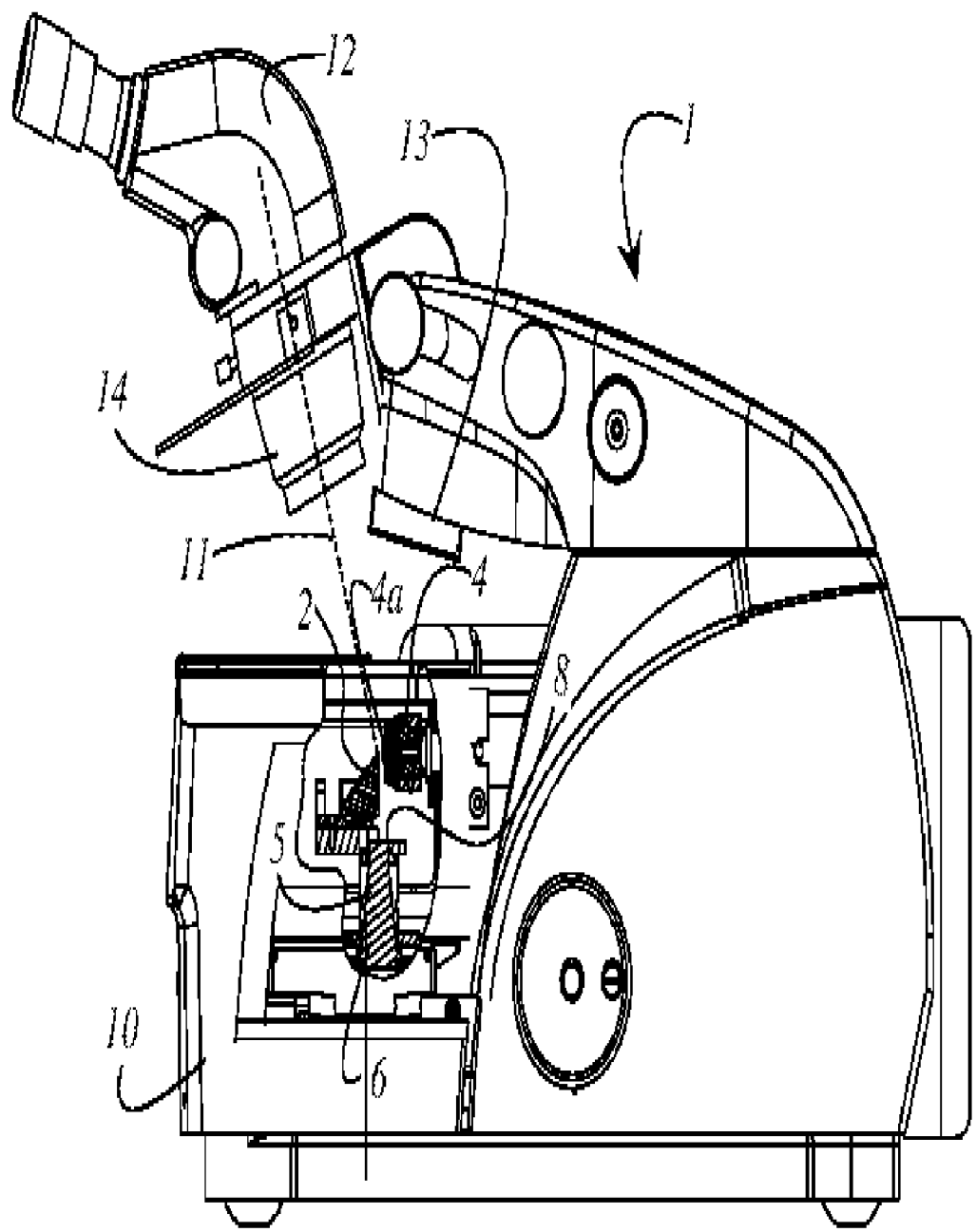
FIG. 1 is a side view of an ultramicrotome with cooling chamber, parts of the cooling chamber being omitted in order to elucidate the association between the knife and sample holder.

FIG. 1 is a side view of a microtome or ultramicrotome 1 having a cooling chamber 10. Parts of cooling chamber 10 are omitted in order to elucidate the association between at least one knife 2 and sample holder 4. The at least one knife 2 is inserted into a knife holder 5. Knife holder 5 is arranged with respect to a base-mounted illumination system 6 in such a way that exit opening 8 of base-mounted illumination system 6 is positioned below knife 2, which is currently in the working position. The working position is defined by the fact that knife 2 is arranged opposite sample holder 4. In the working position, thin sections can be produced with knife 2 from a sample 4a that is clamped in sample holder 4. Base-mounted illumination system 6 is used to achieve an optimum adjustment in the presetting operation between knife 2 and sample 4a. An incident illumination system 13 for cooling chamber 10 is also provided on microtome 1.

Microtome 1 is equipped with a stereomicroscope 12 that comprises an optical system 14. Optical system 14 of stereomicroscope 12 defines an optical axis 11. This configuration results in optimum contrast during alignment of knife 2 with respect to the surface of sample 4a that is to be cut. The provision of base-mounted illumination system 6 means that cutting edge 16 of the respective knife 2 that is in the working position can be better detected and, if necessary, oriented with respect to sample 4a.

Figure 2:
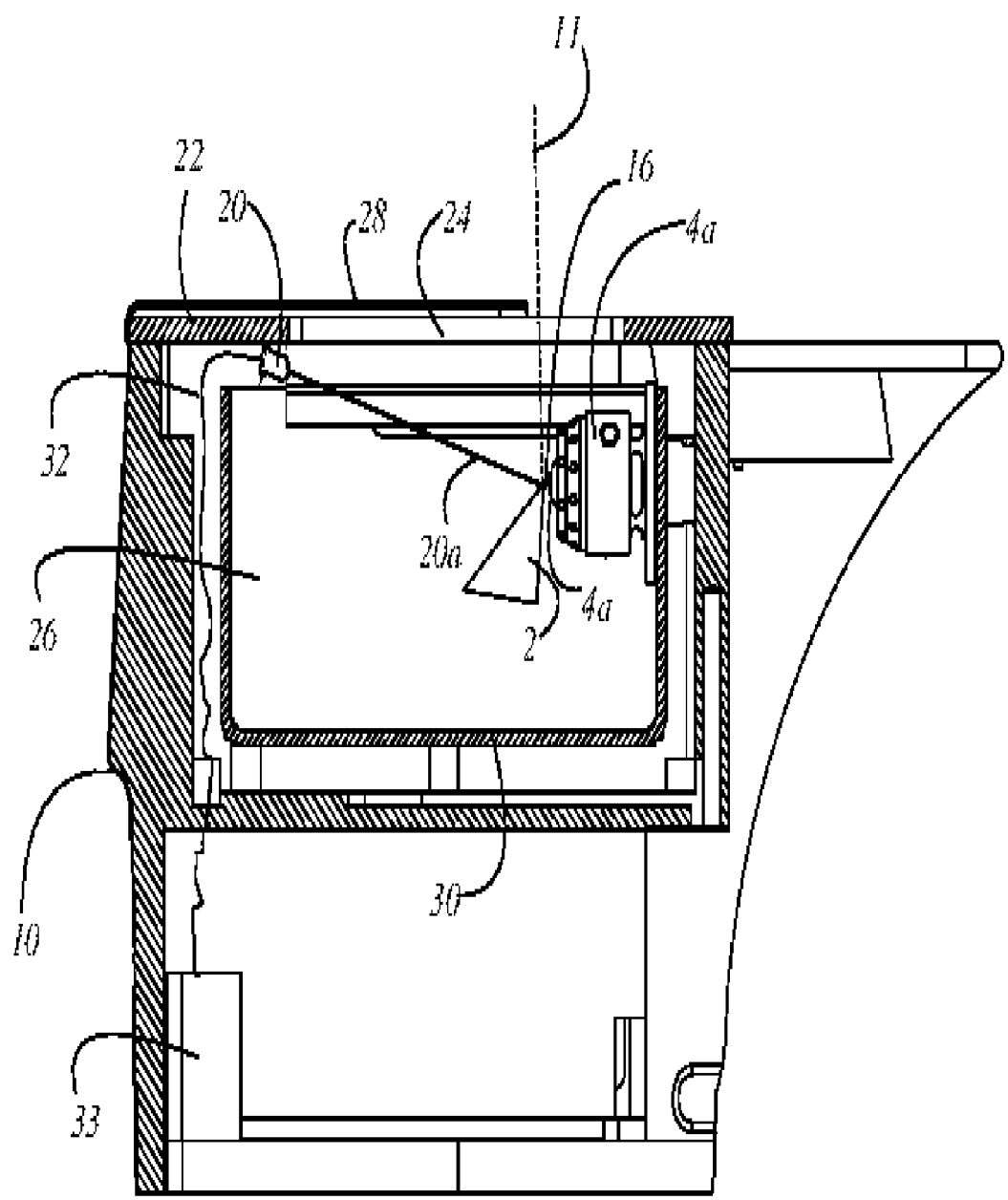
FIG. 2 is a cross section of the cooling chamber, side parts being omitted in order to elucidate the arrangement of the illumination system.

FIG. 2 shows, in addition to incident illumination system 13 that is shown in FIG. 1 (but not shown in FIG. 2), an illumination system 20 housed in cooling chamber 10. Illumination system 20 comprises several LEDs. Cooling chamber 10 is cup-shaped and is closed off by a lid 22. Lid 22 has in it an opening 24 that enables access to interior 26 of cooling chamber 10. In addition, lid 22 is equipped with a further cover 28 to allow the passage of light from incident illumination system 13 into cooling chamber 10. Illumination system 20 is mounted just under or directly under lid 22 of cooling chamber 10. Illumination system 20 is an arrangement of several LEDs whose light 20a is directed onto knife 2. Illumination system 20 is mounted in a region of cooling chamber 10 in which the temperature is sufficiently high for the operation of illumination system 20. The temperature decreases sharply toward base 30 of cooling chamber 10. Illumination system 20 is directed onto knife 2 in such a way that the direction of the reflection at a surface 2a of knife 2 coincides with optical axis 11 of stereomicroscope 12.

Figure 3:
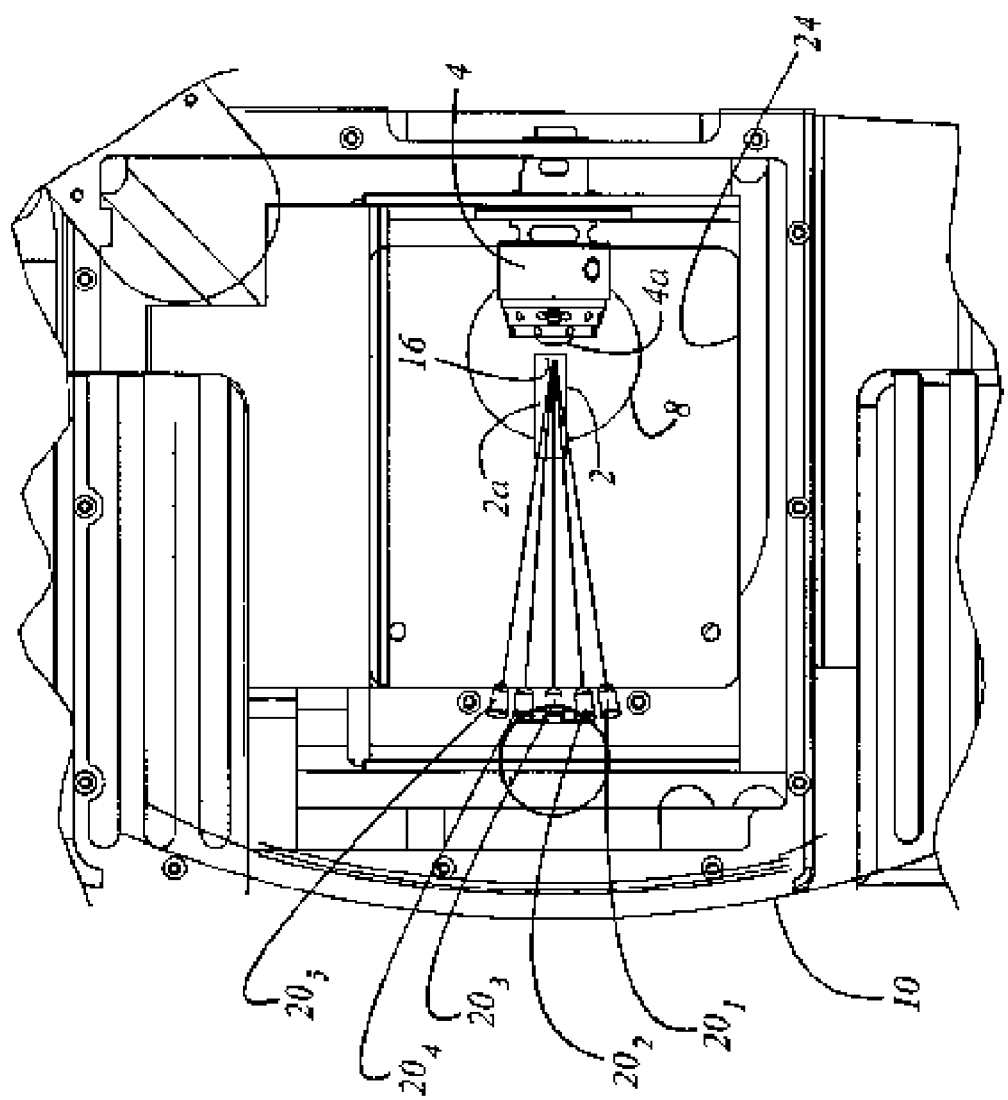
FIG. 3 shows the cooling chamber from above.

FIG. 3 shows cooling chamber 10 from above. An arrangement of a first, second, third, fourth, and fifth LED $20_1$, $20_2$, $20_3$, $20_4$, and $20_5$ is shown here as an exemplary embodiment of illumination system 20. An oblique illumination can be achieved when a segment of illumination system 20 is operated, e.g. by way of first and second LED $20_1$ and $20_2$ or fourth and fifth LED $20_4$ and $20_5$. The number of LEDs and the segmentation of the individual LEDs is not predetermined, and can be adapted to the requisite illumination conditions. Knife 2 has a surface 2a on which the cut sections that are produced come to rest. It is advantageous for the user if surface 2a of knife 2, on which the sections come to rest, reflects light 20a of LEDs $20_1$, $20_2$, $20_3$, $20_4$, and $20_5$ into optical system 14 of stereomicroscope 12. Sections of sample 4a that are resting on this surface 2a of knife 2 are readily detectable. LEDs $20_1$, $20_2$, $20_3$, $20_4$, and $20_5$ and their wiring 32 and control system 33 are located inside cooling chamber 10. Disruption of the gas/air boundary layer is avoided.

What is claimed is:

1. A cooling chamber: comprising an illumination system that emits light, a knife surrounded by the cooling chamber, wherein the knife defines a surface, and a stereomicroscope provided outside the cooling chamber for the observation of the surface of the knife, whereby the illumination system is arranged such that the emitted light is directed onto the surface of the knife in such a way that the light reflects from the surface toward the stereomicroscope.

2. The cooling chamber as defined in claim 1, wherein the illumination system is constructed from several LEDs.

3. The cooling chamber as defined in claim 2, wherein segments of the several LEDs are capable of being switched on and off individually in order to implement an oblique illumination of the surface of the knife.

4. The cooling chamber as defined in claim 2, wherein the illumination system is constructed from a first, a second, a third, a fourth, and a fifth LED.

5. The cooling chamber as defined in claim 4, wherein operation of the first and the second LED implements an oblique illumination of the surface of the knife.

6. The cooling chamber as defined in claim 4, wherein operation of the fourth and the fifth LED implements an oblique illumination of the surface of the knife.

7. The cooling chamber as defined in claim 1, wherein the cooling chamber is cup-shaped and is closed off by a lid having an opening; and the illumination system is mounted directly under the lid of the cooling chamber.

8. A system of a cooling chamber with a microtome, comprising a knife defining a cutting edge, a sample holder, wherein the knife and the sample holder are arranged in the cooling chamber and opposite to each other, a stereomicroscope positioned on the microtome wherein the stereomicroscope defines an optical axis, and the region of the cutting edge of the knife being observable with the stereomicroscope, and an illumination system mounted in the cooling chamber emits light which is directed onto a surface of the knife in such a way that the light reflects from the surface toward the stereomicroscope.

9. The system as defined in claim 8, wherein the light reflects from the surface substantially parallel to an optical axis of the stereomicroscope.

10. The system as defined in claim 8, wherein the illumination system is constructed from several LEDs.

11. The system as defined in claim 10, wherein segments of the several LEDs are capable of being switched on and off individually in order to implement an oblique illumination of the surface of the knife.

12. The system as defined in claim 10, wherein the illumination system is constructed from a first, a second, a third, a fourth, and a fifth LED.

13. The system as defined in claim 12, wherein operation of the first and the second LED implements an oblique illumination of the surface of the knife.

14. The system as defined in claim 12, wherein operation of the fourth and the fifth LED implements an oblique illumination of the surface of the knife.

15. The system as defined in claim 8 wherein the cooling chamber is cup-shaped and is closed off by a lid having an opening; and the illumination system is mounted directly under the lid of the cooling chamber.

16. The system as defined in claim 15 wherein the knife, the surface of the knife, the cutting edge, and the sample holder with the sample are observable through the opening in the lid.

* * * * *